(12) United States Patent
Huang et al.

(10) Patent No.: US 9,682,248 B2
(45) Date of Patent: Jun. 20, 2017

(54) DEEP BRAIN MAGNETIC STIMULATOR

(71) Applicant: University of Rochester, Rochester, NY (US)

(72) Inventors: Jason Haitao Huang, Rochester, NY (US); Samantha Dayawansa, Williamsville, NY (US)

(73) Assignee: University of Rochester, Rochester, NY (US)

( * ) Notice: Subject to any disclaimer, the term of this patent is extended or adjusted under 35 U.S.C. 154(b) by 744 days.

(21) Appl. No.: 14/031,404

(22) Filed: Sep. 19, 2013

(65) Prior Publication Data

US 2014/0081072 A1 Mar. 20, 2014

Related U.S. Application Data

(60) Provisional application No. 61/703,568, filed on Sep. 20, 2012.

(51) Int. Cl.
*A61N 2/00* (2006.01)
*A61N 2/02* (2006.01)

(52) U.S. Cl.
CPC .............. *A61N 2/006* (2013.01); *A61N 2/02* (2013.01)

(58) Field of Classification Search
CPC .............. A61N 1/3605; A61N 1/36064; A61N 1/36067; A61N 1/36071; A61N 1/36075; A61N 1/360078; A61N 1/36096; A61N 1/36082; A61N 1/0529; A61N 1/0534; A61N 2/00; A61N 2/002; A61N 2/004; A61N 2/006; A61N 2/02
See application file for complete search history.

(56) References Cited

U.S. PATENT DOCUMENTS

| | | | |
|---|---|---|---|
| 6,056,767 A * | 5/2000 | Boussignac | A61F 2/958 606/194 |
| 6,086,525 A | 7/2000 | Davey et al. | |
| 6,402,678 B1 | 6/2002 | Fischell et al. | |
| 7,407,478 B2 | 8/2008 | Zangen et al. | |
| 7,658,704 B2 | 2/2010 | Fox et al. | |
| 7,824,324 B2 | 11/2010 | Riehl et al. | |
| 7,857,746 B2 | 12/2010 | Riehl et al. | |
| 7,946,973 B2 | 5/2011 | Peterchev | |
| 7,963,903 B2 | 6/2011 | Ghiron et al. | |
| 7,976,451 B2 | 7/2011 | Zangen et al. | |
| 8,172,742 B2 | 5/2012 | Zheng et al. | |
| 2002/0183829 A1* | 12/2002 | Doscher | A61F 2/82 623/1.15 |

(Continued)

FOREIGN PATENT DOCUMENTS

WO    WO 2010/017249 A1    2/2010

*Primary Examiner* — Charles A Marmor, II
*Assistant Examiner* — Carrie R Dorna
(74) *Attorney, Agent, or Firm* — Patent Technologies, LLC; Robert D. Gunderman, Jr.

(57) ABSTRACT

A deep brain magnetic stimulator is disclosed that is placed within a vessel of the body to provide targeted location specific application of a magnetic field within the brain. The deep brain magnetic stimulator has a stimulation coil affixed to an expandable device core where the device core has a lumen to allow the passage of blood. A source of electrical energy is provided as well as related control circuitry to govern the activation of the stimulation coil and also govern such parameters as magnetic field strength, duration, waveform, and the like.

20 Claims, 9 Drawing Sheets

(56) References Cited

U.S. PATENT DOCUMENTS

| | | | |
|---|---|---|---|
| 2007/0203541 A1* | 8/2007 | Goetz | A61N 1/37247 607/59 |
| 2007/0238984 A1* | 10/2007 | Maschke | A61B 5/0031 600/424 |
| 2009/0069854 A1* | 3/2009 | Keidar | A61M 1/101 607/3 |
| 2009/0105784 A1* | 4/2009 | Massoud-Ansari | A61N 1/36082 607/45 |
| 2009/0234426 A1* | 9/2009 | Pellinen | A61N 1/05 607/116 |
| 2009/0259284 A1* | 10/2009 | Yamasaki | A61B 5/06 623/1.11 |
| 2010/0113959 A1 | 5/2010 | Pascual-Leone et al. | |
| 2010/0228075 A1* | 9/2010 | Lu | A61N 2/008 600/13 |
| 2011/0218381 A1 | 9/2011 | Ruohonen | |
| 2011/0319700 A1 | 12/2011 | Schneider | |
| 2012/0116149 A1 | 5/2012 | Pilla et al. | |

* cited by examiner

DEEP BRAIN MAGNETIC STIMULATOR

CROSS REFERENCE TO RELAXED PATENT APPLICATIONS

This application claims priority to U.S. Patent Application Ser. No. 61/703,568 filed Sep. 20, 2012 entitled "Deep Brain Magnetic Stimulator" by Jason Haitao Huang of Rochester, N.Y. and Samantha Dayawansa of Rochester, N.Y., the entire disclosure of which is incorporated herein by reference.

BACKGROUND OF THE INVENTION

1. Field of the Invention

This invention relates generally to brain stimulation, and more specifically to a deep brain magnetic stimulator.

2. Description of Related Art

External transcranial magnetic brain stimulation (TMS) has been used for several years to treat patients with depression, stroke, multiple sclerosis, Parkinson's disease, and the like. Transcranial magnetic brain stimulation (TMS) is non-invasive, where a magnetic field is generated that in turn induces small electric currents in the brain that change the polarization of neurons in the brain, thus causing activity in certain regions of the brain that may have a therapeutic effect.

An inherent risk from external transcranial magnetic brain stimulation is one of seizures. Other risks include minor pains and discomfort, psychiatric changes, fainting, and syncope. In addition, the application of external transcranial magnetic brain stimulation is limited to a superficial brain area and is typically confined to an area around 1 to 3 centimeters deep to the skull, and completely sparing deeper brain regions. In addition, such an approach cannot be targeted to a specific deep brain area. In addition, the path of the induced current in transcranial magnetic brain stimulation is difficult to predict due to the irregular shape of the brain and the non-uniform conductivity of the brain and surrounding tissue and bone, making targeted treatment, in particular in deep brain areas, difficult if not impossible. In addition, the magnetic field applied in external transcranial magnetic brain stimulation does not reach deeply into the brain, resulting in a surface effect. While a surface effect may be adequate for some therapies, many therapeutic methods require deeper penetration of the brain than is possible with external transcranial magnetic brain stimulation.

BRIEF SUMMARY OF THE INVENTION

In accordance with the present invention, there is provided a deep brain magnetic stimulator comprising a device core capable of being placed in the luminal periphery of a blood vessel without impeding blood flow or causing blood clots. The device core comprises a lumen to allow the passage of blood and walls having expandable folds; a stimulation coil affixed to the device core comprising a conductive element; an energy storage device electrically coupled to the stimulation coil; and control circuitry comprising a power handling module to control the delivery of voltage and current to the stimulation coil, and a control module to control the activation of the stimulation coil.

The foregoing paragraph has been provided by way of introduction, and is not intended to limit the scope of the invention as described in this specification, claims and the attached drawings.

BRIEF DESCRIPTION OF THE DRAWINGS

The invention will be described by reference to the following drawings, in which like numerals refer to like elements, and in which.

Figure 1:
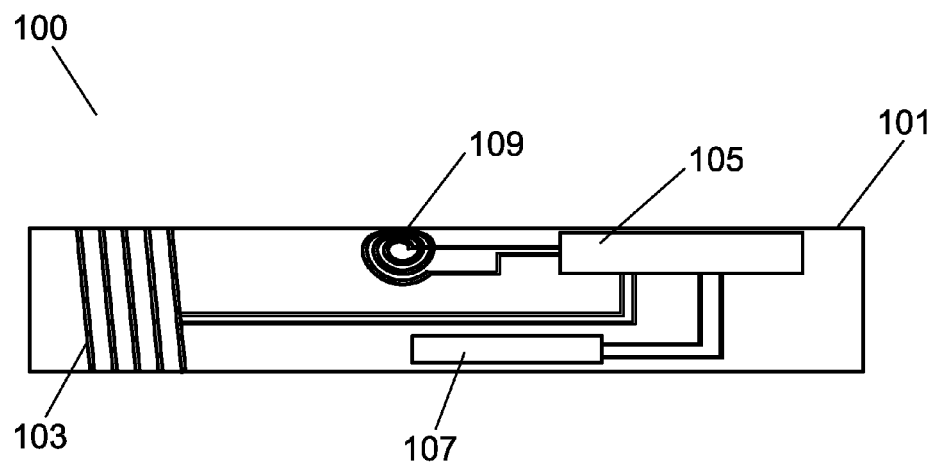
FIG. 1 is a side plan view of the deep brain magnetic stimulator.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by this specification, claims and the attached drawings.

DESCRIPTION OF THE PREFERRED EMBODIMENTS

For a general understanding of the present invention, reference is made to the drawings. In the drawings, like reference numerals have been used throughout to designate identical elements.

The present invention will be described by way of example, and not limitation. Modifications, improvements and additions to the invention described herein may be determined after reading this specification and viewing the accompanying drawings; such modifications, improvements, and additions being considered included in the spirit and broad scope of the present invention and its various embodiments described or envisioned herein.

The deep brain magnetic stimulator as described and depicted herein has applications that include facilitation of stroke recovery, management of intractable Parkinson's Disease, stroke and spinal trauma management in conjunction with stem cells to facilitate cell migration and subsequent functional restoration, multiple sclerosis management in deep brain areas, management of Alzheimer's patients, and inhibition of a seizure nidus to control intractable epilepsy without surgery. In addition, the deep brain magnetic stimulator will allow management of intractable depression, schizophrenia, muscle spasms, and the like.

Figure 2:
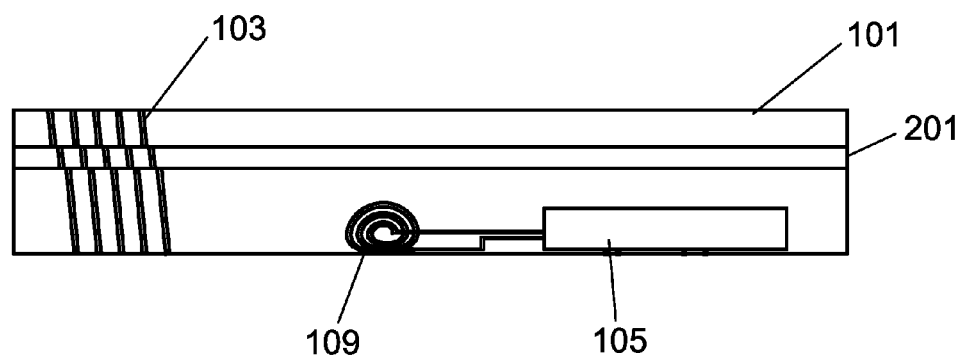
FIG. 2 is a rotated side plan view of the deep brain magnetic stimulator.

Referring to the present invention in detail, in FIG. 1 there is shown a side plan view of the deep brain magnetic stimulator 100. A device core 101 can be seen in FIG. 1 as a generally tubular structure that is capable of being placed within a blood vessel where the device core has a lumen to allow the passage of blood once deployed. The device core 101 may, in one embodiment of the present invention, be from 1 to 15 French in outer diameter (where one French=⅓ millimeter) and have an overall length of from about 4 millimeters to about 30 millimeters in length. Other embodiments of the present invention may employ other geometries. The device core may be made of various biocompatible materials such as, for example, stainless steel, tantalum, cobalt chromium, nitinol, shape memory polymers, or the like. The device core 101 is made in a manner similar to that of a stent. In some embodiments of the present invention, the device core is coated with silicon carbide to reduce platelet and leukocyte adhesion. In some embodiments of the present invention, the device core is coated with a drug-eluting coating such as, for example, heparin, paclitaxel, sirolimus, or the like, to prevent fibrosis and development of thrombus. The device core 101 may be made by processes used to manufacture other forms of metal tubing. For example, metal sheets are folded and welded end to end to create a metal tube. That metal tube is then extruded into smaller diameter tubes. The folds or other expandable elements may be placed in the device core either before attachment of the ends or after. In some embodiments of the present invention, the device core is extruded and drawn to the proper diameter. The device core 301 has an expandable structure such as a scaffold structure or folds 201 that will either self-expand with the use of a shape-memory material such as nitinol (nickel titanium) or can be expanded through the use of a balloon catheter. The folds 201 as shown in FIG. 2 (not shown in FIG. 1) traverse the length of the device core 101, and may vary in number and size depending cm parameters such as patient specific vessel size, location in the vessel, overall size of the deep brain magnetic stimulator, and the like. Both scaffold structures and expandable folds are considered expandable elements, and allow the deep brain magnetic stimulator to be placed in a blood vessel or similar structure and be expanded by various techniques that will be further described herein. The expandable folds 201 of the device core 101 are, in one embodiment of the present invention, generally parallel to the longitudinal axis of the device core. The longitudinal axis of the device core 101 is generally parallel to the flow of blood through the device core 101. In its non-deployed or folded state, the device core 101 is of a lesser diameter than the diameter of the device core when the folds are expanded. In one embodiment of the present invention, the folds overlap one another to achieve optimal packing efficiency and size reduction in a non-deployed state. Such an arrangement can be clearly seen in FIG. 4. Each fold has an angle in relation to a radius of a circle. Each fold, when made in the device core, creates a first fold wall and a second fold wall. The first fold wall and the second fold wall are generally parallel to each other. The first fold wall and the second fold wall join at a point closer to the center of the device core than the circumference of the device core. The area in which the first fold wall and the second fold wall join may have a radius or similar curvature to allow the device core to expand upon deployment. In some embodiments of the present invention, this area has a null curvature, meaning that It abruptly changes from the first fold wall to the second fold wall, in other words, it is a sharp crease or fold. The stimulation coil may, in some embodiments of the present invention, traverse the folds and be shaped with and conform to the specific geometry of the folds, as depicted again in FIG. 4.

Also seen in FIG. 1 is the stimulation coil 103 that comprises a conductive element that is wound or otherwise configured in loops or turns to generate a magnetic field when an electrical current flows through it. The conductive element may be copper, iron, silver, gold, or the like. The conductive element may be a single strand of material, or, in some embodiments of the present invention, may comprise several smaller strands of conductive material that may, in some embodiments of the present invention, be insulated from one another. The conductive element that makes up the stimulation coil 103 may further be coated with a biocompatible coating. The stimulation coil 103 may be wound around the device core 101, or, in some embodiments of the present invention, may be a flat spiral coil that is affixed to the wall of the device core 101. Other orientations of the stimulation coil 103 that may include spacers, shims, stand-offs, ancillary fixtures, and the like, may be employed to provide a directional component to the magnetic (B) field that may be desirable for a specified therapeutic effect. In other words, the stimulation coil 103 may be attached to the device core 101 using attachment means that provide a directional component to the generated magnetic (B) field of the stimulation coil 103. Further, in some embodiments of the present invention, the stimulation coil 103 may be wound around a ferromagnetic core such as an iron core, a composite layered iron core, or the stimulation coil 103 may be wound around a magnetic core. The ferromagnetic or magnetic core may also be integrated with, or circumferential to, the device core 101. Appropriate insulators between the conductive element and the device core 101, and any ferromagnetic or related magnetic core materials, are utilized to ensure proper stimulation coil operation.

The strength of the magnetic (B) field generated by the stimulation coil 103 is proportional to the number of turns of the conductive element that make up the stimulation coil 103 and also the electrical current provided to the stimulation coil 103. These two variables make up the magnetomotive force (MMF) of the stimulation coil 103.

To activate the stimulation coil, an electrical current is applied. An energy storage device 107 is shown in FIG. 1 that is coupled or otherwise affixed to the device core 101. The energy storage device 107 is electrically coupled to the stimulation coil 103. In some embodiments of the present invention, the energy storage device 107 is operatively coupled to control circuitry 105 mat may include a power handling module to control delivery of voltage and current to the stimulation coil, and may also include, in some embodiments of the present invention, a control module to control the activation of the stimulation coil. The current and voltage delivered to the stimulation coil may be pulsed, modulated, or otherwise contain a frequency component to deliver a changing or time-varying magnetic field. For example, near rectangular pulses with controllable pulse width may be desirable for some therapeutic applications. The control circuitry employs miniaturization techniques such as microelectronic design and packaging, hybrid circuit design and packaging, and the like. The energy storage device 107 may be a battery, or may be a capacitor such as an ultracapacitor or the like. Suitable batteries include, but are not limited to, lithium ion implantable batteries or other microbatteries that are implantable. To charge the energy storage device 107, a charging coil 109 may be employed that provides inductively coupled charging from an external source of electromagnetic radiation. Such an arrangement is described in United States Patent Application Publication US2009/0289595 A1 to Chen et al. and entitled "Wireless Charging Module and Electronic Apparatus", the entire disclosure of which is incorporated herein by reference. The charging coil 109 is made from a conductive material such as copper, and may be coiled or formed as a spiral. The conductive material may further be a wire, flat stock, printed conductive film, or the like. In addition, in some embodiments of the present invention, an energy harvesting device such as a MEMS device or a piezoelectric device to convert kinetic energy of the body into electrical energy is used to charge the energy storage device 107.

FIG. 2 is an axially rotated side plan view of the deep brain magnetic stimulator 100 showing the folds 201 in the device core 101. The folds are present when the deep brain magnetic stimulator is in an unexpanded state. There may be a single fold, or a plurality of folds. In addition, a scaffold structure similar to that used for stents may be employed in addition to, or in place of, the folds 201. The deep brain magnetic stimulator 100 may be deployed using a balloon catheter, or, with suitable self-expanding materials for the device core 101 (for example, nitinol), with a sleeve style catheter for deployment of a self-expanding deep brain magnetic stimulator. The folds may be generally v-shaped or u-shaped, or they may angled and folded to accommodate a greater expansion ratio upon deployment. The expansion ratio as defined herein is the ratio of the expanded outer diameter of the deep brain magnetic stimulator to the unexpanded outer diameter of the deep brain magnetic stimulator. Placement of the stimulation coil 103, control circuitry 105, energy storage device 107 (see FIG. 1), and charging coil 109 may vary along with actual geometries of these components, dependent on the specific requirements of the deep brain magnetic stimulator to be deployed.

Figure 3:
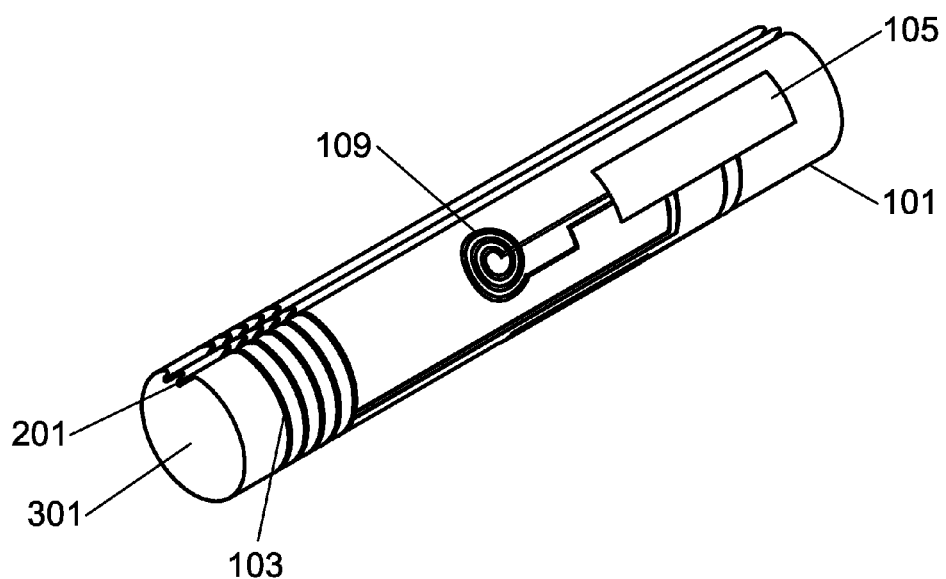
FIG. 3 is a perspective view of the deep brain magnetic stimulator.
Figure 4:
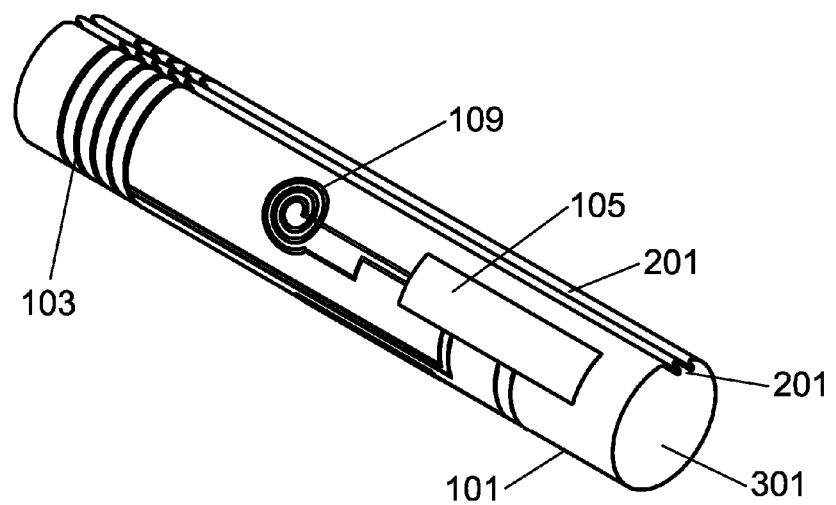
FIG. 4 is another perspective view of the deep brain magnetic stimulator.

FIG. 3 is a perspective view of the deep brain magnetic stimulator in an unexpanded state and FIG. 4 is another perspective view of the deep brain magnetic stimulator also in an unexpanded state.

Figure 5:
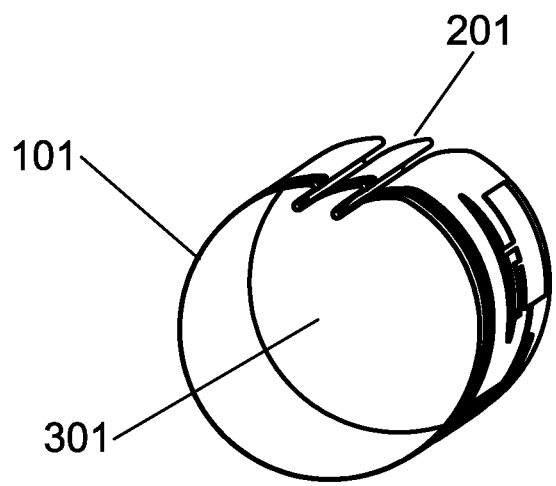
FIG. 5 is an end perspective view of the deep brain magnetic stimulator.

To better show the exemplary folds 201 in the device core 101, FIG. 5 is an end perspective view of the deep brain magnetic stimulator in an unexpanded state showing the folds 201 in the device core 101 and the lumen 301 that is created by way of the fundamental structure of the device core 101.

Figure 6:
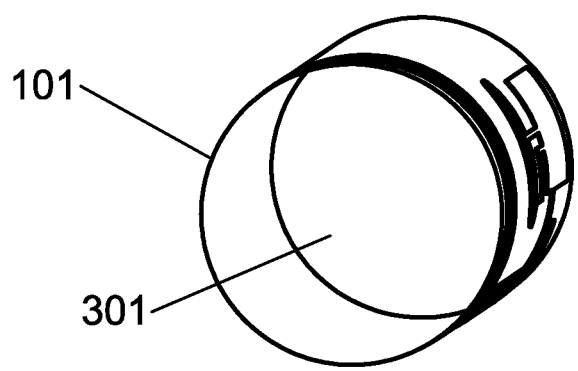
FIG. 6 is an end perspective view of the deep brain magnetic stimulator in an expanded state.

FIG. 6 is an end perspective view of the deep brain magnetic stimulator in an expanded state. Once the deep brain magnetic stimulator is deployed and expanded by either mechanical means such as by attachment to a balloon catheter, or through the use of self-expanding or shape retaining materials such as nitinol (nickel titanium) and a corresponding sleeve style catheter, the folds 201 are either gone or deformed in such as way that the diameter of the lumen 301 increases from that of the deep brain magnetic stimulator in an unexpanded state.

Figure 7:
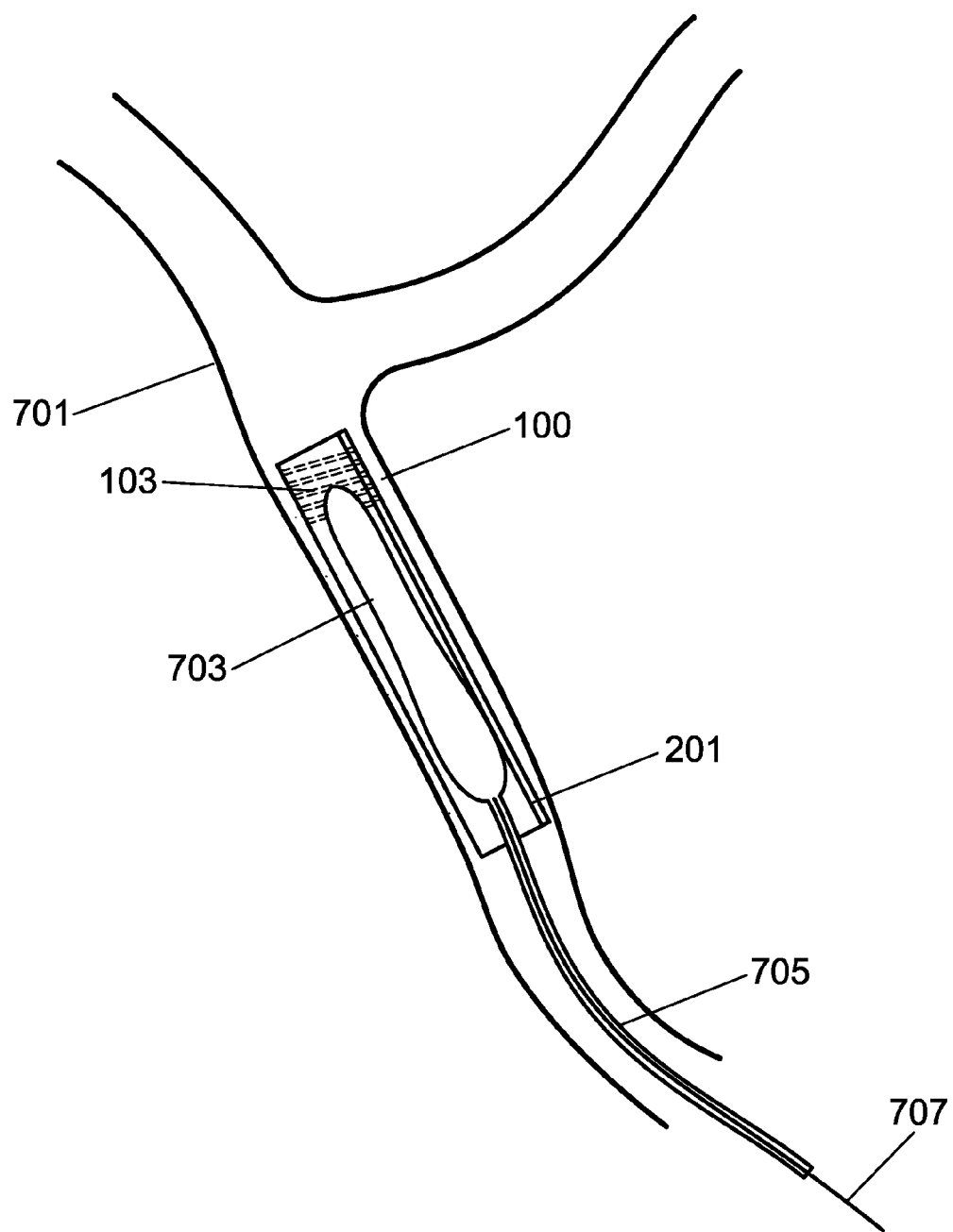
FIG. 7 depicts the deep brain magnetic stimulator being deployed in an unexpanded state.
Figure 8:
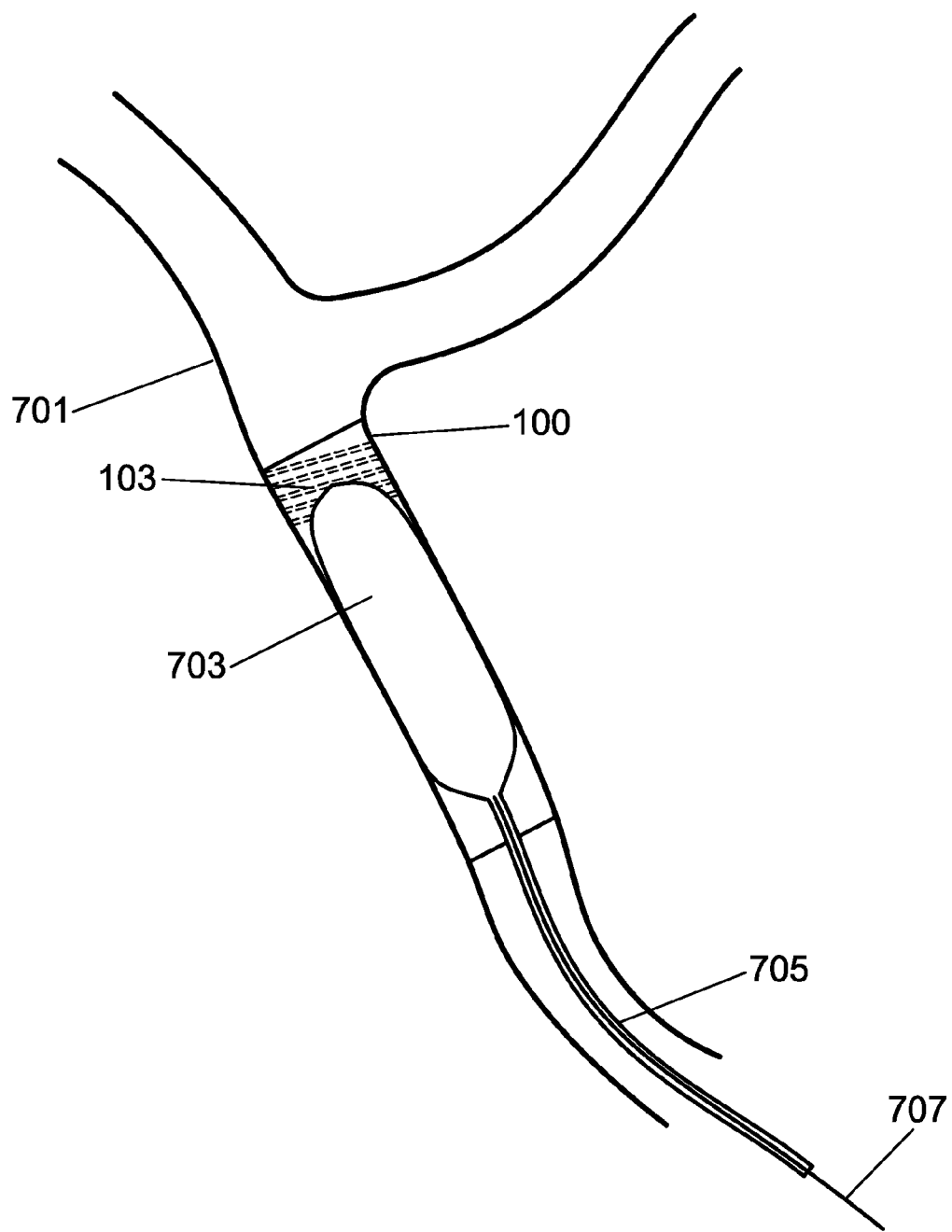
FIG. 8 depicts the deep brain magnetic stimulator being deployed in an expanded state.
Figure 9:
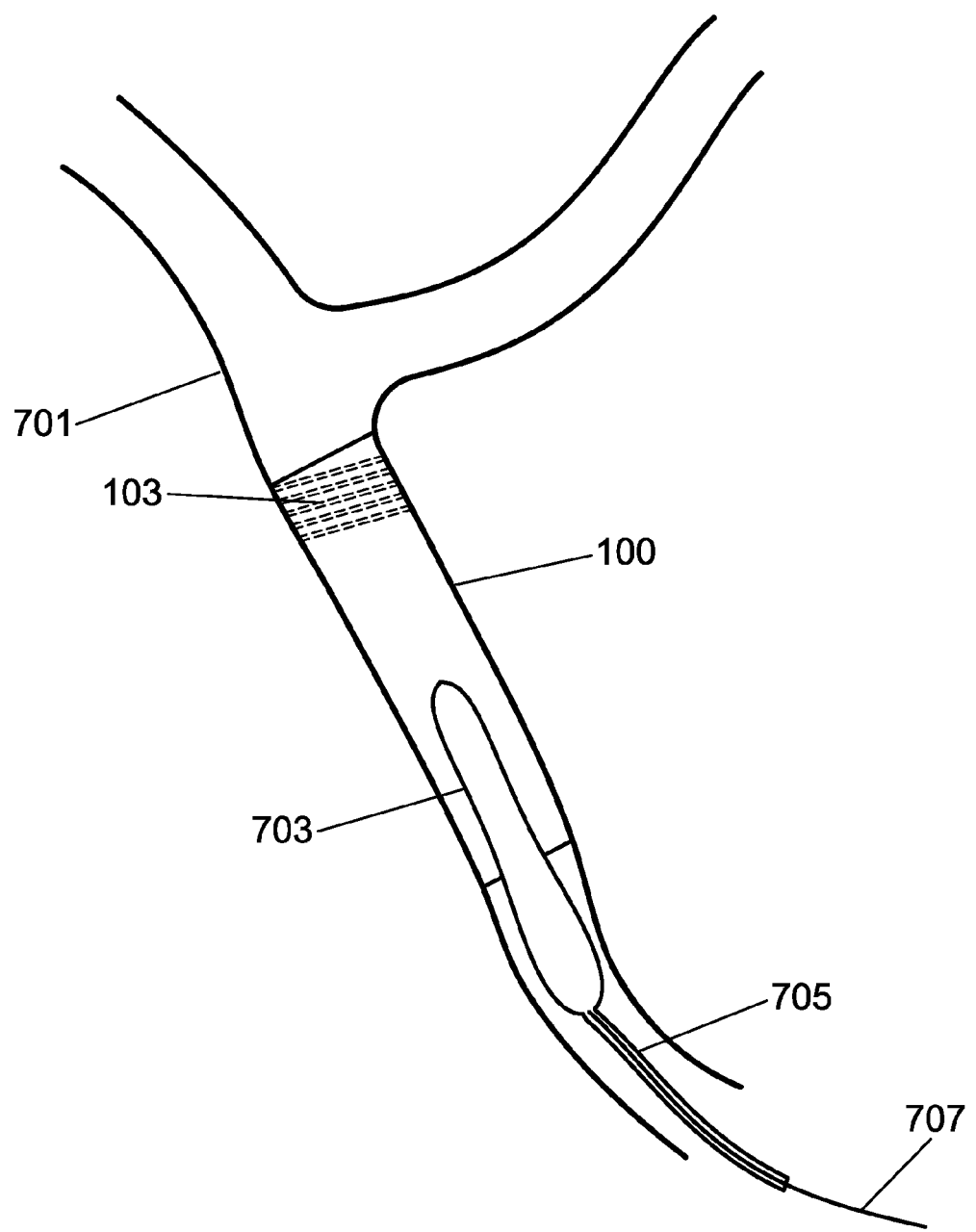
FIG. 9 depicts the deep brain magnetic stimulator in an expanded state with the catheter being removed.
Figure 10:
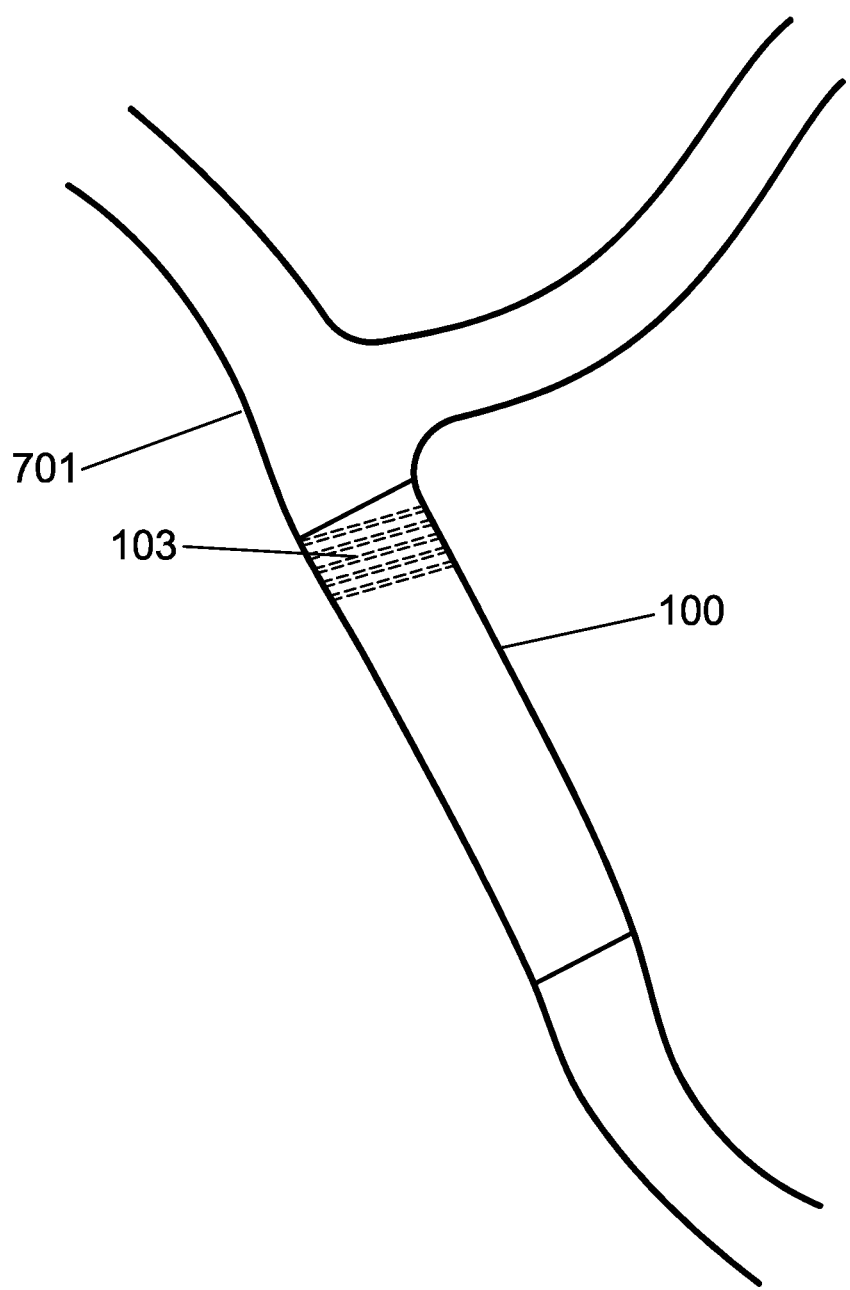
FIG. 10 depicts the deep brain magnetic stimulator in an expanded and operational state.

FIG. 7 depicts the deep brain magnetic stimulator being deployed in an unexpanded state. To implant the deep brain magnetic stimulator, the deep brain magnetic stimulator 100 is attached to a catheter 707. Prior to insertion of the deep brain magnetic stimulator 100 with the attachment catheter, a dilation procedure may take place to assist with securing the deep brain magnet stimulator 100 in place. FIG. 7 shows the folds 201 in an unexpanded state. In one embodiment of the present invention, the catheter 707 is a balloon catheter. FIG. 7 illustrates a balloon catheter with a balloon 703 placed within the device core. A tube 705 is in fluid communication with the balloon 703; the tube 705 being attached to a pump or other pressure generating device for subsequent inflation of the balloon 703. The deep brain magnetic stimulator 100 is guided by the catheter 707 through a vessel 701 until proper placement is determined through the assistance of angiography, intravascular ultrasound (IVUS) or the like. In guiding the catheter 707 through the vessel 701, a contrast material may also be used to aid in imaging. Once the deep brain magnetic stimulator 100 is in proper position, the balloon 703 is inflated by way of the tube 705 and related pump (pump not depicted in FIG. 8), and the pressure from the expanding balloon 703 unfolds the deep brain magnetic stimulator. FIG. 8 depicts the deep brain magnetic stimulator being deployed in an expanded state. In FIG. 8, the balloon 703 has been inflated, the folds are no longer prevalent, and the lumen of the deep brain magnetic stimulator 100 has enlarged to conform to the vessel walls. Once the deep brain magnetic stimulator 100 has been expanded in position, the balloon 703 is deflated, as shown in FIG. 9, and the catheter is removed. This leaves the deep brain magnetic stimulator in an expanded and operational state, as shown in FIG. 10. In an alternative embodiment, the device core 101 is self-expanding, and is made from a shape memory material such as nitinol (nickel titanium). A self-expanding device core 101 reduces or eliminates the need for a balloon catheter, and instead relies on a sleeved arrangement where the deep brain magnetic stimulator 100 is deployed within a sleeve that is subsequently removed once the deep brain magnetic stimulator 100 is in the proper location, upon which time the device core 101 expands and is secured in place within the vessel.

It should be noted that FIGS. 7-10 show only the stimulation coil 103; the control circuitry and related energy storage device and charging coil are on the backside of the deep brain magnetic stimulator, and cannot be seen in these Figures.

Figure 11:
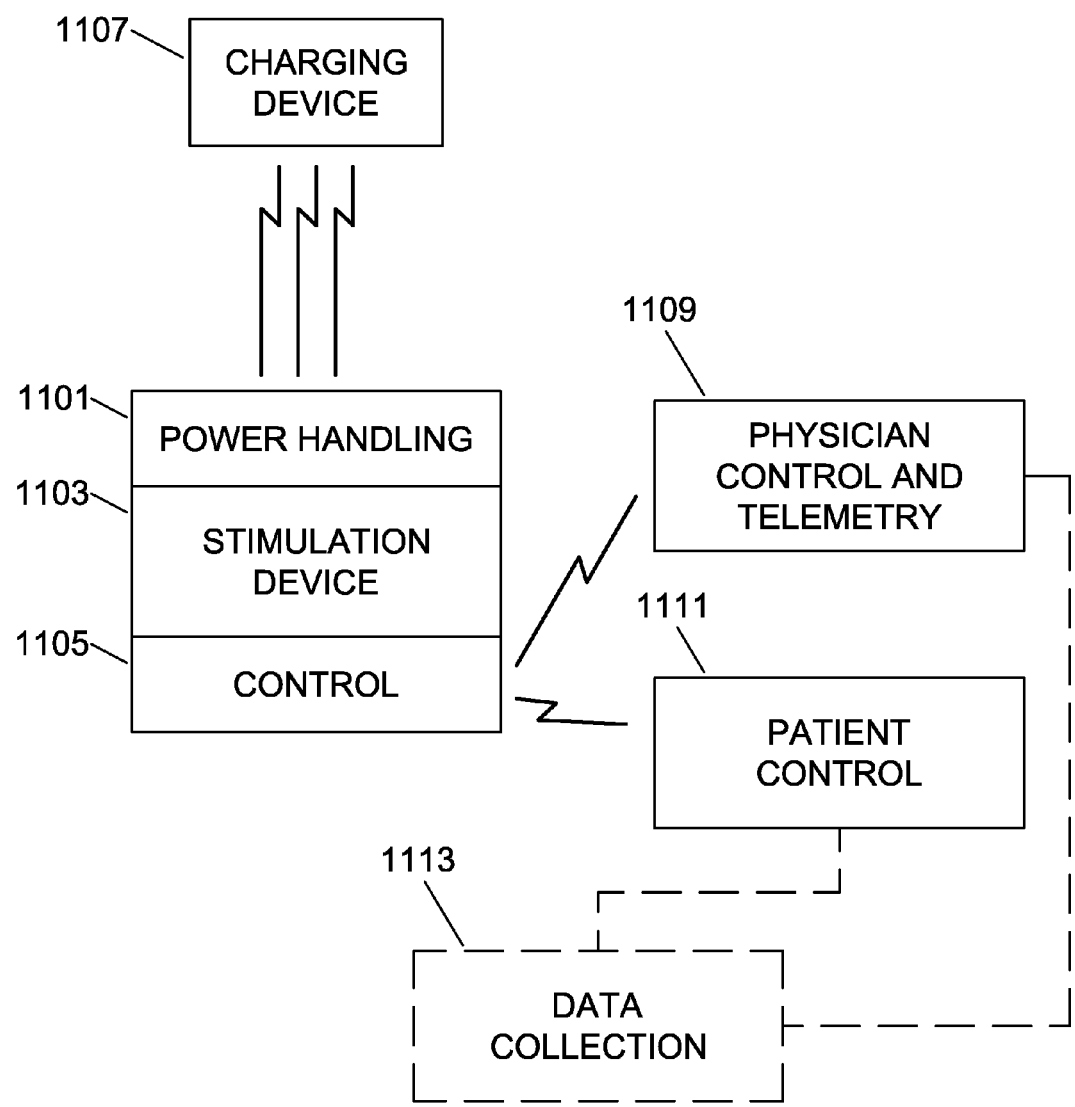
FIG. 11 is a block diagram depicting electrical/electronic functions of the deep brain magnetic stimulator.

FIG. 11 Is a block diagram depicting electrical/electronic functions of the deep brain magnetic stimulator. A power handling module 1101 receives power from the charging coil that in operation is inductively coupled to an external source of electromagnetic radiation. When a charging device 1107 that provides electromagnetic radiation through a coil or similar structure is placed in proximity to the implanted deep brain magnetic stimulator, the magnetic field that originates from the coils in the charging device 1107 causes a current to How in the charging coil. The power handling module 1101 senses this induced current flow in the charging coil, and provides regulation of both the current and the voltage from the charging coil to provide regulated and conditioned electrical power to the energy storage device. The power handling module 1101 allows for adequate charging of the energy storage device, and provides conditioning, charge and discharge control, and other such functions to maintain the energy storage device in proper working order. In addition, the power handing module 1101 controls the delivery of power to the stimulation device 1103 that comprises the stimulation coil. A control module 1105 provides a wireless interface to both external physician control and telemetry 1109 and patient control 1111. Patient control 1111 may include a remote device for activating the stimulation device 1103 (energizing the stimulation coil, for example), adjusting the amplitude of the magnetic (B) field, modulating the magnetic (B) field, changing the frequency of the magnetic (B) field, and the like. Such changes in the magnetic (B) field that are generated by the stimulation coil can be correlated to desired therapeutic effects. Such correlations may take place within the patient control device 1111 by way of a relational database or similar topology. Patient control 1111 is limited in order to ensure the safety of the patient. Physician control and telemetry 1109 provides for a greater range of operational parameters in the areas of activating the stimulation device 1103 (energizing the stimulation coil, for example), adjusting the amplitude of the magnetic (B) field, modulating the magnetic (B) field, changing the frequency of the magnetic (B) field, and the like. In addition, as telemetry function is provided that logs the specified operational parameters and the resulting patient outcomes. The resulting patient outcomes may include data 1113 collected from other diagnostic instruments, or it may be data that is input by the patient related to their condition before and after the change of any given operational parameter. This aspect of the present invention is very important to the development of improved treatment protocols, as deep brain magnetic stimulation in accordance with the present invention is novel and presents an opportunity to develop a myriad of treatment regimens with the proper data.

A system for deep brain magnetic stimulation can thus be manufactured which includes the deep brain magnetic stimulator and a physician control and telemetry device in wireless communication with the control module of the deep brain magnetic stimulator. A data storage device for retaining operational data of the deep brain magnetic stimulator may also be provided in this system such that there is historical information related to the treatment protocols used. The treatment protocols include the magnitude and duration of a magnetic field, as well as other optional variables such as direction of the magnetic field that may be used in embodiments of the present invention that allow one to adjust the direction of the magnetic field by specific orientation of the stimulation coils, multiple stimulation coils that can be addressed and selectively energized to provide a directional field, and the like. The system for deep brain magnetic stimulation may also comprise a patient control device in wireless communication with the deep brain magnetic stimulator where the patient can control the application of a magnetic field, the magnitude of the magnetic field, the duration of the magnetic field, the orientation of the magnetic field, and the like.

Figure 12:
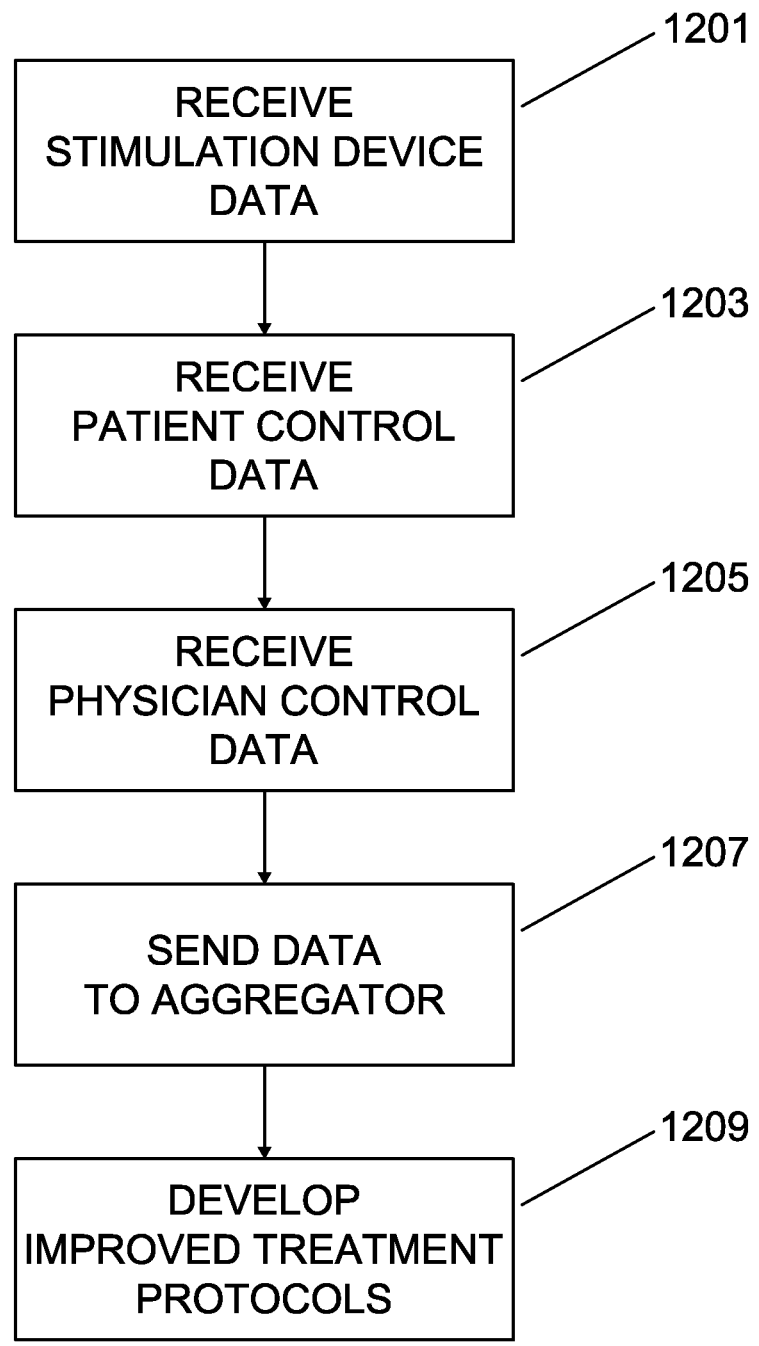
FIG. 12 is a flowchart depicting a method for developing improved treatment protocols for the deep brain magnetic stimulator.

FIG. 12 is a flowchart depicting a method for developing improved treatment protocols for the deep brain magnetic stimulator. The stimulation device and related control circuitry may also collect data related to the activation of the stimulation coil, the amplitude, frequency, and any modulation parameters related to the excitation waveform applied to the stimulation coil, and various other parameters that relate to the generation of an electromagnetic field from the deep brain magnetic stimulator. Further, patient control data and physician control data may be correlated to the stimulation device data as well as data related to the efficacy of the various treatment protocols and sent to an aggregator that collects and processes data from a plurality of deep brain magnetic stimulators in order to develop improved treatment protocols. As depicted in the flowchart of FIG. 12, stimulation device data is received in step 1201, patient control data is received in step 1203, physician control data is received in step 1205, the collected data is sent to an aggregator in step 1207 and improved treatment protocols are developed by correlating the collected and aggregated data in step 1209. Such methods may be used to develop improved treatment protocols by obtaining relevant data from a patient population to determine trends that can be used to develop improved treatment protocols, such as the use of specific magnetic field amplitudes and durations for the treatment of a specific ailment. An exemplary method for developing Improved treatment protocols for deep brain magnetic stimulation comprises the steps of receiving on a computer magnetic stimulation event information from a deep brain magnetic stimulator, the information comprising magnitude of magnetic stimulation, duration of magnetic stimulation, and date and time of magnetic stimulation; receiving on a computer body function information from a patient comprising body function metrics that correlate to the date and time of a magnetic stimulation event; correlating on a computer a unique patient identifier to the magnetic stimulation event information and the body function information; correlating on a computer the magnetic stimulation event information and the body function information by patient identifier and date and time; and identifying on a computer trends between patients to develop improved treatment protocols.

While the various objects of this invention have been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of this specification, claims and the attached drawings.

What is claimed is:

1. A deep brain magnetic stimulator comprising:
 a device core capable of being placed in a luminal periphery of a blood vessel where the device core is generally tubular in shape and comprises a lumen to allow the unassisted passage of blood and a lumen wall having expandable elements;
 a stimulation coil affixed to the device core comprising a conductive element, wherein the stimulation coil is disposed around the entire outer circumference of the device core;
 the stimulation coil configured to generate a non-revolving magnetic field;
 an energy storage device electrically coupled to the stimulation coil to deliver voltage and current to the stimulation coil without resonance of the stimulation coil with the energy storage device; and
 control circuitry comprising a power handling module to control the delivery of voltage and current to the stimulation coil, and a control module to control activation of the stimulation coil.

2. The deep brain magnetic stimulator of claim 1, wherein the expandable elements are stent scaffolding elements.

3. The deep brain magnetic stimulator of claim 1, wherein the expandable elements are expandable folds.

4. The deep brain magnetic stimulator of claim 3, wherein the expandable folds of the device core are generally parallel to the longitudinal axis of the device core and when folded create a device core of a lesser diameter than the diameter of the device core when the folds are expanded.

5. The deep brain magnetic stimulator of claim 1, wherein the outer diameter of the device core is from about 1 French to about 15 French.

6. The deep brain magnetic stimulator of claim 1, wherein the overall length of the device core is from about 4 millimeters to about 30 millimeters.

7. The deep brain magnetic stimulator of claim 1, wherein the device core is selected from the group consisting of stainless steel, tantalum, cobalt chromium, nitinol, and shape memory polymers.

8. The deep brain magnetic stimulator claim 1, further comprising a silicon carbide coating on the device core.

9. The deep brain magnetic stimulator of claim 1, further comprising a drug-eluting coating on the device core.

10. The deep brain magnetic stimulator of claim 9, wherein the drug-eluting coating is selected from the group consisting of heparin, paclitaxel, and sirolimus.

11. The deep brain magnetic stimulator of claim 1, wherein the stimulation coil is made from a conductive element selected from the group consisting of copper, iron, silver and gold.

12. The deep brain magnetic stimulator of claim 1, further comprising a biocompatible coating on the stimulation coil.

13. The deep brain magnetic stimulator of claim 1, further comprising a ferromagnetic core where the conductive element of the stimulation coil is wound around said ferromagnetic core.

14. The deep brain magnetic stimulator of claim 1, further comprising a magnetic core where the conductive element of the stimulation coil is wound around said magnetic core.

15. The deep brain magnetic stimulator of claim 1, wherein the energy storage device is a capacitor.

16. The deep brain magnetic stimulator of claim 1, further comprising a charging coil in electrical communication with the energy storage device.

17. A system for deep brain magnetic stimulation comprising:
the deep brain magnetic stimulator of claim 1;
a physician control and telemetry device in wireless communication with the control module of the deep brain magnetic stimulator; and
a data storage device for retaining operational data of the deep brain magnetic stimulator.

18. The system for deep brain magnetic stimulation of claim 17, further comprising a patient control device in wireless communication with the deep brain magnetic stimulator.

19. A deep brain magnetic stimulator comprising:
a device core capable of being placed in a luminal periphery of a blood vessel where the device core is generally tubular in shape and comprises a lumen to allow the unassisted passage of blood and a lumen wall having expandable element, wherein the stimulation coil is disposed around the entire outer circumference of the device core;
a stimulation coil affixed to the device core comprising a conductive element;
the stimulation coil configured to generate a non-revolving magnetic field;
a battery electrically coupled to the stimulation coil; and
control circuitry comprising a power handling module to control the delivery of voltage and current to the stimulation coil, and a control module to control activation of the stimulation coil.

20. A method for developing improved treatment protocols for deep brain magnetic stimulation comprising the steps of:
receiving on a computer magnetic stimulation event information from
a deep brain magnetic stimulator comprising:
a device core capable of being placed in a luminal periphery of a blood vessel where the device core is generally tubular in shape and comprises a lumen to allow the unassisted passage of blood and a lumen wall having expandable elements;
a stimulation coil affixed to the device core comprising a conductive element;
the stimulation coil configured to generate a non-revolving magnetic field;
an energy storage device electrically coupled to the stimulation coil; and
control circuitry comprising a power handling module to control delivery of voltage and current to the stimulation coil, and a control module to control activation of the stimulation coil;
the information comprising magnitude of magnetic stimulation, duration of magnetic stimulation, and date and time of magnetic stimulation;
receiving on the computer body function information from a patient comprising body function metrics that correlate to the date and time of a magnetic stimulation event;
correlating on the computer a unique patient identifier to the magnetic stimulation event information and the body function information;
correlating on the computer the magnetic stimulation event information and the body function information by patient identifier and date and time; and
identifying on the computer trends between patients to develop improved treatment protocols.

\* \* \* \* \*

UNITED STATES PATENT AND TRADEMARK OFFICE
CERTIFICATE OF CORRECTION

PATENT NO. : 9,682,248 B2  Page 1 of 1
APPLICATION NO. : 14/031404
DATED : June 20, 2017
INVENTOR(S) : Jason Haitao Huang et al.

It is certified that error appears in the above-identified patent and that said Letters Patent is hereby corrected as shown below:

In the Claims

Column 9, Line 36, Claim 19, 'having expandable element,' should read -having expandable elements,-

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*